United States Patent
Della Santina et al.

(10) Patent No.: US 9,289,598 B2
(45) Date of Patent: Mar. 22, 2016

(54) VESTIBULAR STIMULATION ELECTRODE

(71) Applicants: MED-EL Elektromedizinische Geraete GmbH, Innsbruck (AT); The Johns Hopkins University, Baltimore, MD (US)

(72) Inventors: Charles Coleman Della Santina, Towson, MD (US); Andreas Marx, Innsbruck (AT)

(73) Assignees: MED-EL Elektromedizinische Geraete GmbH, Innsbruck (AT); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/180,431

(22) Filed: Feb. 14, 2014

(65) Prior Publication Data
US 2014/0228926 A1 Aug. 14, 2014

Related U.S. Application Data

(60) Provisional application No. 61/764,631, filed on Feb. 14, 2013.

(51) Int. Cl.
*A61N 1/00* (2006.01)
*A61N 1/05* (2006.01)
*A61N 1/36* (2006.01)

(52) U.S. Cl.
CPC ............ *A61N 1/0541* (2013.01); *A61N 1/0526* (2013.01); *A61N 1/0551* (2013.01); *A61N 1/361* (2013.01); *A61N 1/36032* (2013.01)

(58) Field of Classification Search
CPC . A61N 1/0526; A61N 1/0551; A61N 1/0541; A61N 1/361; A61N 1/36032
See application file for complete search history.

(56) References Cited

U.S. PATENT DOCUMENTS 6,304,787 B1 10/2001 Kuzma
2008/0312717 A1* 12/2008 Gantz .............................. 607/57
(Continued)

FOREIGN PATENT DOCUMENTS

EP 2108398 12/2010
EP 1496983 11/2012
(Continued)

OTHER PUBLICATIONS

International Searching Authority, Authorized Officer Blaine R. Copenheaver, International Search Report and Written Opinion— PCT/US2014/016363, mailed May 6, 2014, 10 pages.
(Continued)

*Primary Examiner* — Michael Kahelin
*Assistant Examiner* — Mallika D Fairchild
(74) *Attorney, Agent, or Firm* — Sunstein Kann Murphy & Timbers LLP

(57) ABSTRACT

A vestibular stimulation electrode lead is described for conducting electrical stimulation signals generated by an implanted vestibular stimulation module. An extra-vestibular lead branch carries the stimulation signals from the stimulation module to a vestibular entry location. A stopper collar is bent away at a first discrete angle from a distal end of the extra-vestibular lead branch to penetrate into a vestibular structure at the entry location. An intra-vestibular electrode array is bent away at a second discrete angle from the stopper collar and has an outer surface with one or more electrode contacts for delivering the stimulation signals to vestibular neural tissue at a target location within the vestibular structure. The first and second discrete angles form a geometry of the stopper collar and intra-vestibular electrode array that limits insertion of the intra-vestibular electrode array beyond the target location within the vestibular structure.

6 Claims, 7 Drawing Sheets

(56) References Cited

U.S. PATENT DOCUMENTS

| | | | |
|---|---|---|---|
| 2011/0224682 A1 | 9/2011 | Westlund | |
| 2012/0022616 A1 | 1/2012 | Garnham et al. | 607/60 |
| 2012/0078337 A1 | 3/2012 | Darley et al. | 607/136 |
| 2012/0130465 A1* | 5/2012 | Risi et al. | 607/137 |
| 2012/0277835 A1* | 11/2012 | Della Santina et al. | 607/62 |

FOREIGN PATENT DOCUMENTS

| | | |
|---|---|---|
| EP | 2349464 | 10/2013 |
| WO | WO 2010035149 | 4/2010 |
| WO | WO 2010135783 | 12/2010 |
| WO | WO 2012134834 | 10/2012 |

OTHER PUBLICATIONS

Scinicariello et al (2001) Enhancing human balance control with galvanic vestibular stimulation. Biol Cybern 84:475-480.

Eshraghi et al (2012) Biomedical engineering principles of modern cochlear implants and recent surgical innovations. Anat Rec (Hoboken). Nov. 2012;295(11):1957-66. doi: 10.1002/ar.22584. Epub Oct. 8, 2012.

Nguyen et al (2013) Evolution of electrode array diameter for hearing preservation in cochlear implantation. Acta Otolaryngol. Feb. 2013;133(2):116-22. doi: 10.3109/00016489.2012.723824. Epub Dec. 7, 2012.

\* cited by examiner

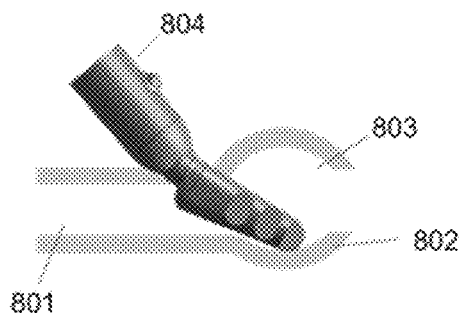 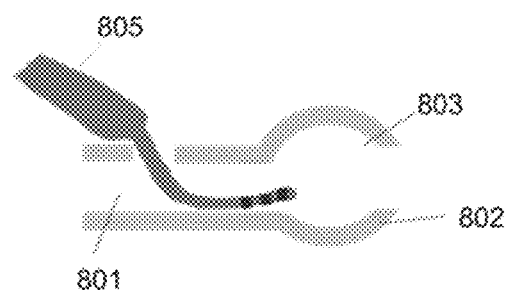
*Fig. 8A*          *Fig. 8B*
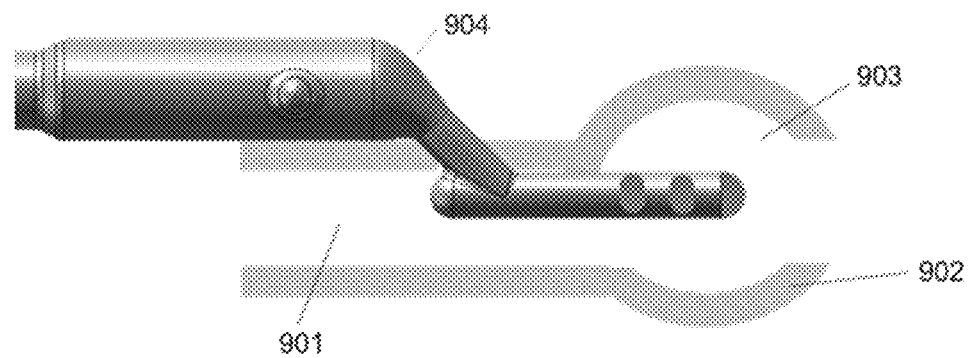
*Fig. 9*

# VESTIBULAR STIMULATION ELECTRODE

This application claims priority from U.S. Provisional Patent Application 61/764,631, filed Feb. 14, 2013, which is incorporated herein by reference in its entirety.

TECHNICAL FIELD

The present invention relates to vestibular implant systems, and specifically a stimulation electrode for such systems.

BACKGROUND ART

The balance sensing functionality of the brain is developed based on neural signals from the vestibular structures of the inner ear, one on each lateral side of the body. As shown in FIG. 1, each inner ear vestibular labyrinth 100 has five sensing organs: the ampullae 108 of the three semi-circular canals—the horizontal (lateral) canal 103, the posterior canal 104, and the superior canal 105—which sense rotational movement, and the utricle 106 and the saccule 107 in the vestibule 102, which sense linear movement.

FIG. 2 shows anatomical detail within a vestibular canal ampulla 108 which is connected at one end to the canal 206 and at the other end to the vestibule 205, and which contains endolymph fluid. The vestibular nerve endings 204 connect to the crista hair cells 203, the cilia ends 202 of which are embedded in the gelatinous cupula 201. When the head moves, the endolymph fluid within the ampulla 108 defects the cupula 201, generating a sensing signal in the vestibular nerve endings 204 that is interpreted by the brain as the sense of balance.

Unfortunately some people suffer from damaged or impaired vestibular systems. Such vestibular dysfunction can cause balance problems such as unsteadiness, vertigo and unsteady vision. Delivery of electrical stimulation to the vestibular system is currently under research to treat patients suffering from vestibular related pathologies. Experimental results indicate that electrical stimulation of the vestibular system has the potential to restore vestibular function, at least partially. See, e.g., Rubinstein J T et al., *Implantation of the Semicircular Canals With Preservation of Hearing and Rotational Sensitivity: A Vestibular Neurostimulator Suitable for Clinical Research*, Otology & Neurology 2012; 33:789-796 (hereinafter "Rubinstein"); Chiang B et al., *Design and Performance of a Multichannel Vestibular Prosthesis That Restores Semicircular Canal Sensation in Rhesus Monkey*; IEEE Trans. Neural Systems and Rehab Engineering 2011; 19(5):588-98 (hereinafter "Merfeld"); and Gong W at al., *Vestibulo-Ocular Responses Evoked Via Bilateral Electrical Stimulation of the Lateral Semicircular Canals*, IEEE Transactions On Biomedical Engineering, Vol. 55, No. 11, November 2008 (hereinafter "Della Santina"); all incorporated herein by reference.

One challenge in developing a vestibular implant is the design of a device-to-body interface, the stimulation electrode. Such a vestibular stimulation electrode needs to selectively stimulate at least one of the vestibular nerve branches for the vestibular canal ampullae. Typically insertion of the stimulation electrode is though the semicircular canal. The stimulation electrode should be located as close as possible to the nerve fibers of the hair cells in the ampulla crista without damaging them.

Currently, different research groups are working on the development of different vestibular implants, with intra-labyrinthine stimulation approaches being of interest for the present purposes. The Merfeld group has described different electrode types using simple wires as stimulation electrodes. This research group has also described the development of polyimide thin film electrodes for a vestibular prosthesis, though no published data with results is available of this kind of electrode. See Hoffmann K P et al., *Design of Microelectrodes for a Vestibular Prosthesis*, BMT 2011 Rostock, Germany (incorporated herein by reference).

The Rubinstein research group published details of a vestibular stimulation electrode in the previously cited Rubinstein article, as well as in U.S. Patent Publication 2012130465 and PCT Patent Publication WO 2010138915 (incorporated herein by reference). Their stimulation electrode, as shown in FIG. 3, has a relatively small diameter to prevent compression of the membranous canals using "soft surgery" techniques. They claim to have developed a vestibular stimulation electrode that allows post-surgical preservation of the natural function of the vestibular system.

The Della Santina research group published details of their stimulation electrode in the previously cited Chiang reference, as well as in U.S. Pat. No. 7,647,120 and PCT Patent Publication WO 2011088130 (FIG. 4) (all incorporated herein by reference). Their prosthesis is being developed for treatment of bilateral vestibular hypofunction (BVH) for which there is no absolute need to preserve natural vestibular function. The research and development strategy here accepts compression or other trauma to the membranous labyrinth in order to get the stimulation electrodes closer to the respective nerve branches. Since the membranous duct fills out almost the entire ampulla, it is virtually impossible to reach the crista without compressing or otherwise traumatizing the membranous canals. FIG. 4 shows this stimulation electrode which uses three active branches each with three electrode contacts. Two of the electrode branches are combined together to form a double forked structure. Two reference electrodes also are used: a "distant reference" for placement on the skull under the temporalis muscle, and an "intralabyrithine reference" for placement inside the common crus (the common part of the superior and posterior canals).

SUMMARY

Embodiments of the present invention are directed to a vestibular stimulation electrode lead for conducting electrical stimulation signals generated by an implanted vestibular stimulation module. An extra-vestibular lead branch carries the stimulation signals from the stimulation module to a vestibular entry location. A stopper collar is bent away at a first discrete angle from a distal end of the extra-vestibular lead branch to penetrate into a vestibular structure at the entry location. An intra-vestibular electrode array is bent away at a second discrete angle from the stopper collar and has an outer surface with one or more electrode contacts for delivering the stimulation signals to vestibular neural tissue at a target location within the vestibular structure. The first and second discrete angles form a geometry of the stopper collar and intra-vestibular electrode array that limits insertion of the intra-vestibular electrode array beyond the target location within the vestibular structure.

In further specific embodiments, the intra-vestibular electrode array has at least three electrode contacts. The vestibular structure may include a vestibular canal ampulla, specifically, the posterior canal ampulla. And the electrode lead may forms a non-chiral shape.

Embodiments of the present invention also include a vestibular implant system having one or more electrode leads according to any of the foregoing.

BRIEF DESCRIPTION OF THE DRAWINGS

FIG. 8 A-B show insertion geometries of a vestibular electrode according to the prior art.

FIG. 9 shows insertion geometry of a vestibular electrode according to an embodiment of the present invention.

DETAILED DESCRIPTION

Embodiments of the present invention are directed to an implantable vestibular electrode that satisfies the many difficult technical challenges which is configured to fit to the human anatomy and allow convenient surgical handling and insertion. Specific embodiments avoid problems of over-insertion and migration of the stimulation electrode, and the mechanical properties of the electrode can be specifically tailored according to the surgeon's needs; for example, stiffness, ductility, malleability and shape memory effects.

Figure 1:
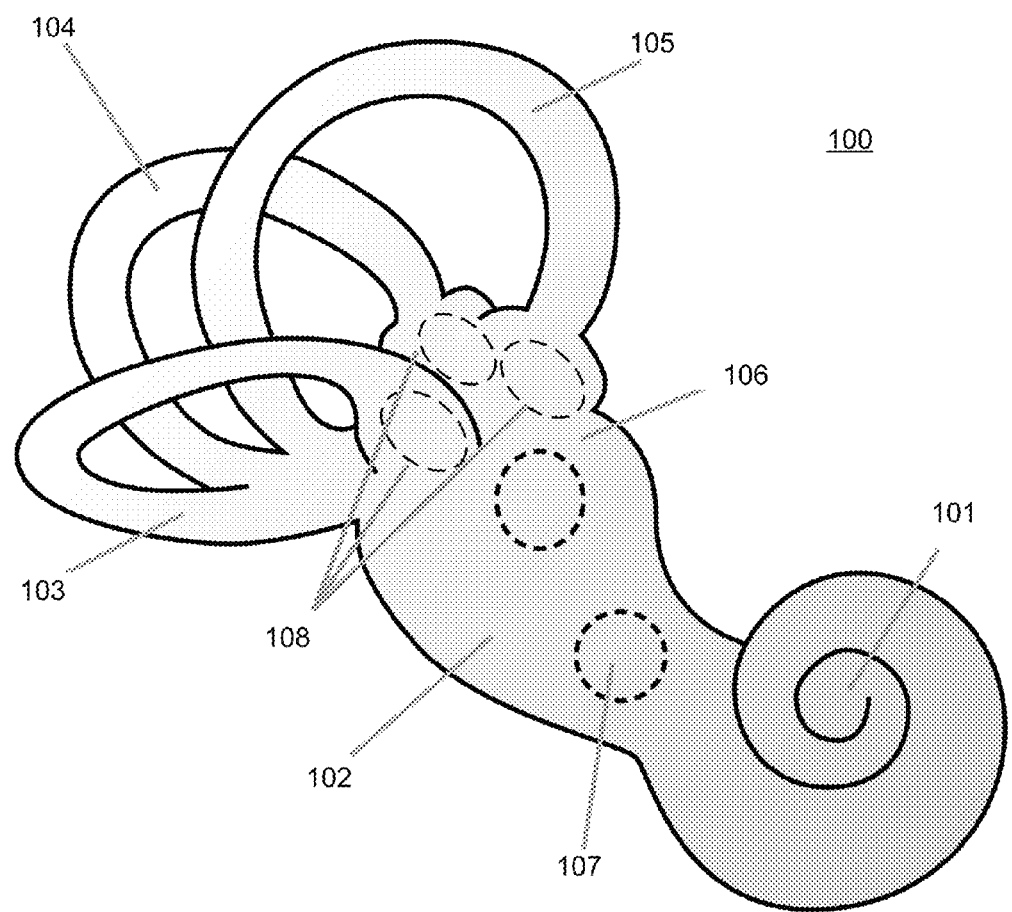
FIG. 1 shows the vestibular labyrinth of the inner ear.
Figure 2:
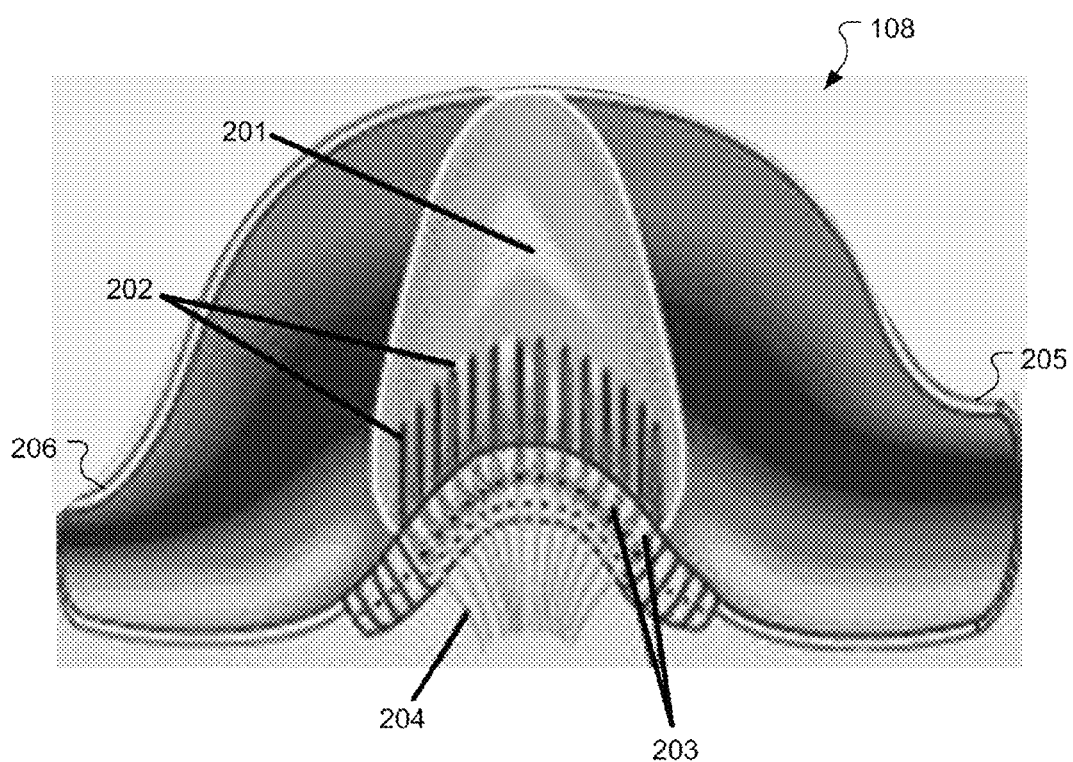
FIG. 2 shows anatomical detail of a vestibular canal ampulla.
Figure 3:
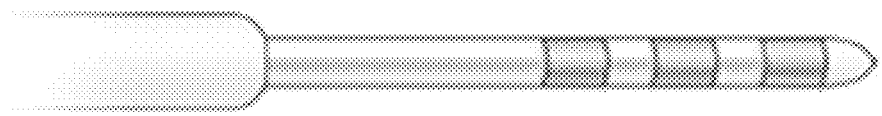
FIG. 3 shows an example of a prior art vestibular stimulation electrode.
Figure 4:
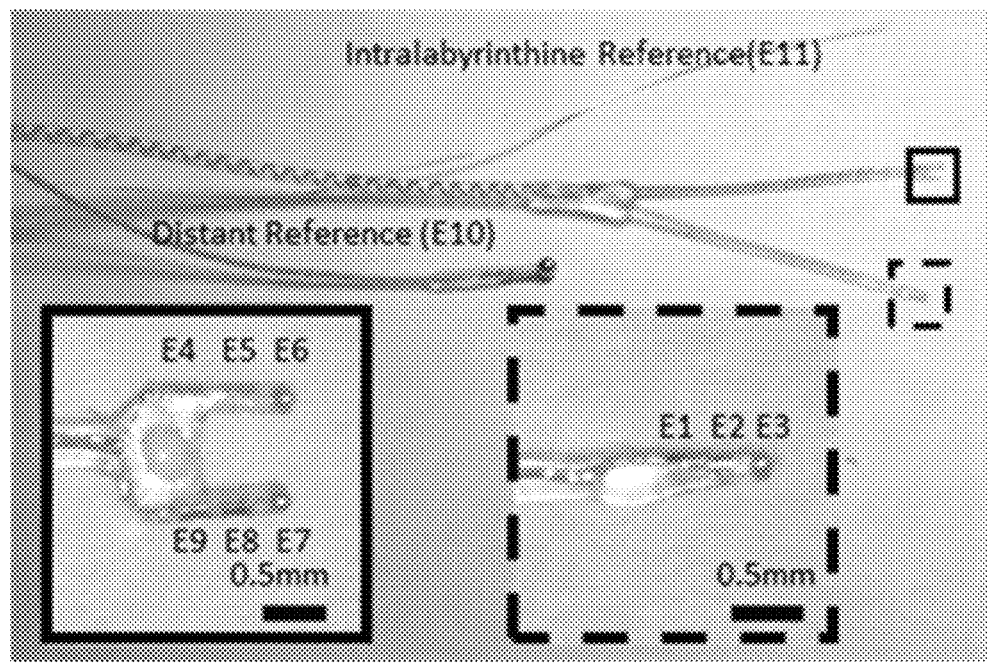
FIG. 4 shows an example of another prior art vestibular stimulation electrode.
Figure 5:
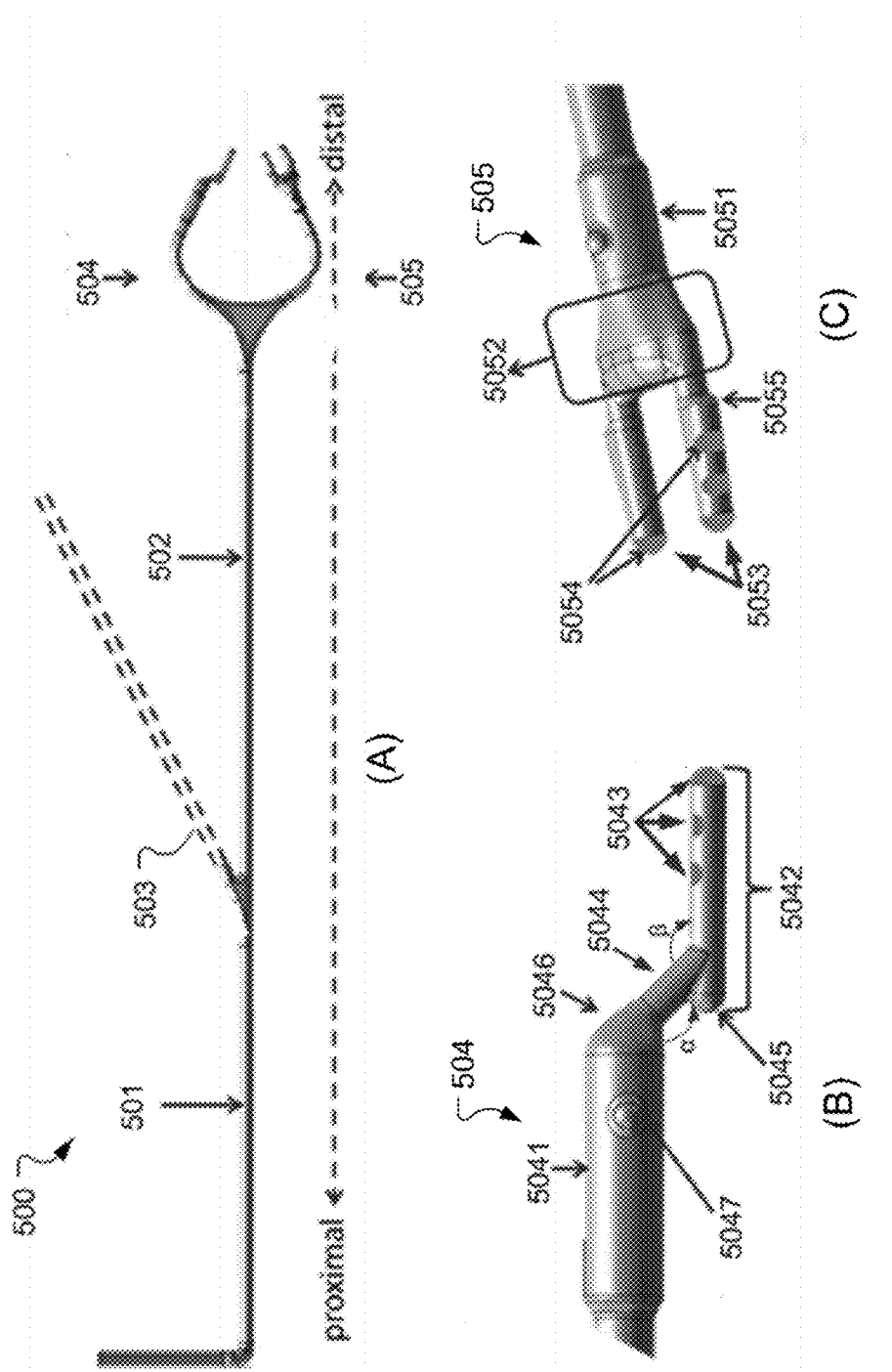
FIG. 5 A-C shows an example of a vestibular stimulation electrode according to one embodiment of the present invention.

FIG. 5 A-C shows an example of a vestibular stimulation electrode 500 according to one embodiment of the present invention that conducts electrode stimulation signals generated by an implanted vestibular stimulation module (not shown). As seen in FIG. 5A, the proximal end of the vestibular stimulation electrode 500 is a single common electrode lead 501 that connects to the stimulation module and which at one point branches in two to provide for a common crus reference electrode 503 (not shown) and an extra-vestibular lead branch 502 carries the stimulation signals from the stimulation module towards a vestibular entry location outside the vestibular labyrinth. The extra-vestibular lead branch 502 bifurcates at the distal end into a single array branch 504 and a double array branch 505.

FIG. 5B shows the single array branch 504 in greater detail showing it has a double bend structure that is configured for insertion into the posterior canal ampulla. An end hub 5041 includes an orientation indicator 5047 and a stopper end 5046. A stopper collar 5044 is bent away at a first discrete angle α from the stopper end 5046 at the distal end of the single array branch 504 to penetrate into a vestibular structure at the vestibular entry location. An intra-vestibular electrode array 5042 is bent away at a second discrete angle β from the stopper collar 5044 at a heel end 5045 and has an outer surface with one or more electrode contacts 5043 for delivering the stimulation signals to vestibular neural tissue at a target location within the vestibular structure.

The first and second discrete angles α and β form a geometry of the stopper collar 5044 and intra-vestibular electrode array 5042 that limits insertion of the intra-vestibular electrode array 5042 beyond the target location within the vestibular structure. The intra-vestibular electrode array 5042 has at least three electrode contacts 5043 to choose from after implantation to provide the ability to compensate for varying anatomies and variations in implantation depth. The double bend structure of the single array branch 504 not only limits over-insertion, but also prevents post-implantation migration and ensures that after implantation the intra-vestibular electrode array 5042 will be parallel to the canal in which it is inserted. The mechanical properties of the single array branch 504 and its double bend structure can be customized by embedding other control materials into the silicone body material.

In a preferred embodiment end hub 5041 runs substantially parallel to the posterior canal after insertion of electrode array 5042 insertion into the posterior canal. Further, end hub 5041 and vestibular electrode array 5042 may be substantially parallel with respect to each other. In another preferred embodiment heel end 5045 may extend beyond the stopper collar 5044 but in opposite direction to the vestibular electrode array 5042.

FIG. 5C shows the double array branch 505 in greater detail including a base hub 5051 and stopper bridge 5052 that form a forked shape with two intra-vestibular branch arrays 5053 with one or more electrode contacts 5054 that is configured for insertion into the lateral and superior canal ampullae that are located adjacent to each other. End bumps 5055 limit the post-surgical outward withdrawal of the electrode branches 5053 from the canal ampullae. The geometry of the double array branch 505 predefines the distance between the two intra-vestibular branch arrays 5053 to an anatomically optimal value that simplifies handling during surgical insertion and prevents over-insertion beyond the intended target locations.

The single branch intra-vestibular electrode array 5042 and the double branch intra-vestibular branch arrays 5053 are ergonomically pre-shaped that they fit to the anatomy of the vestibular structures. This also improves surgical handling, once one of the arrays is implanted the other arrays will automatically be close to their intended insertion location. The electrode 500 also is implemented without chirality to obviate the need for specific left-ear and right-ear versions. A 120° design of the bifurcation between the single branch intra-vestibular electrode array 5042 and the double branch intra-vestibular branch arrays 5053 optimizes the overall mechanical properties the electrode 500 and makes it less prone to wire breakage at the bifurcation.

Figure 6:
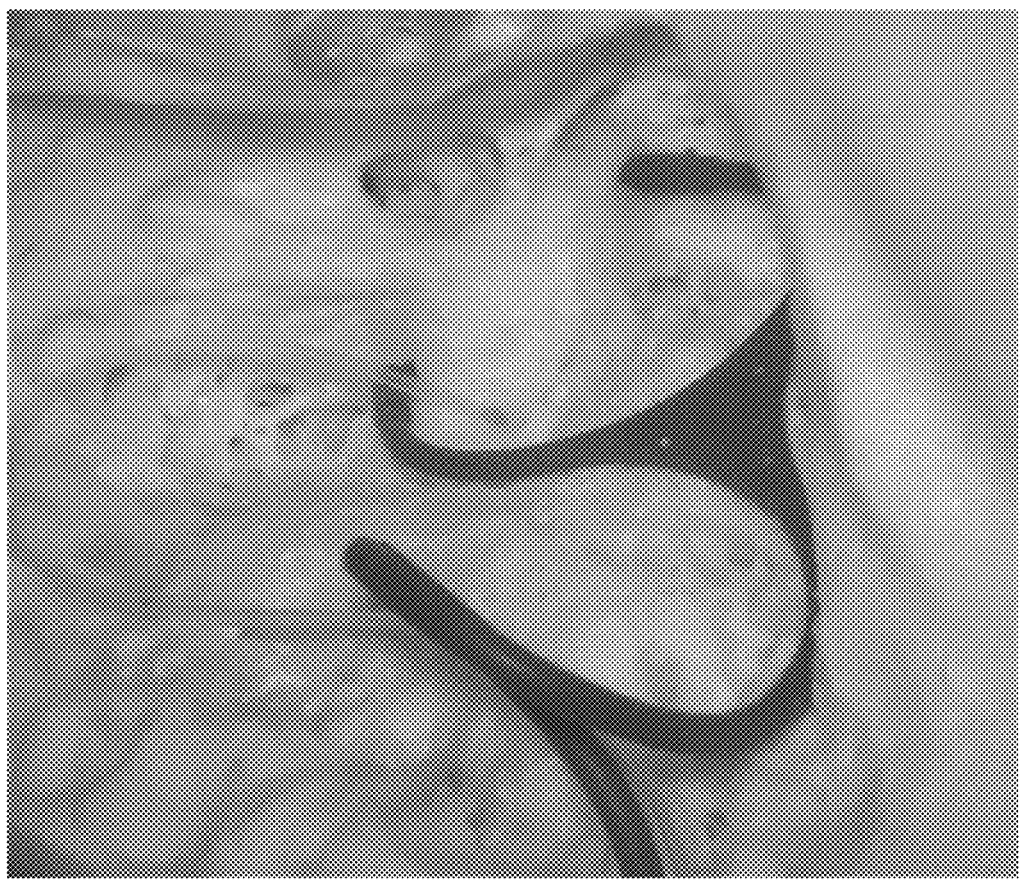
FIG. 6 shows a photograph of an implanted vestibular stimulation electrode according to an embodiment of the present invention.

FIG. 6 shows a photograph of a vestibular stimulation electrode according to an embodiment of the present invention which has been implanted into the vestibular structures at the temporal bone. The ergonomic design minimizes torque and force from the extra-vestibular portions of the electrode lead to the implanted electrode arrays.

Figure 7:
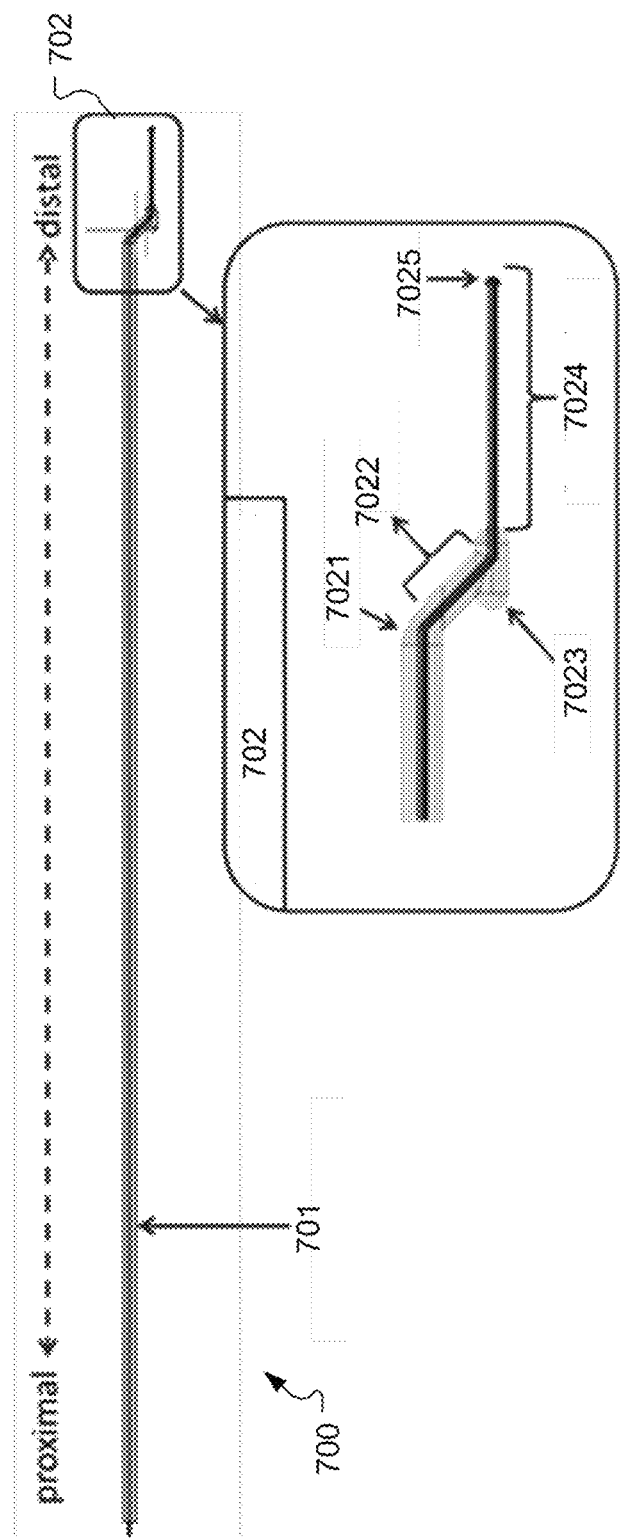
FIG. 7 shows an example of a reference vestibular electrode according to an embodiment of the present invention.

FIG. 7 shows an example of a reference vestibular electrode 700 according to an embodiment of the present invention. In this case, the reference vestibular electrode 700 is a common crus electrode which is suitable for insertion either into the vestibular labyrinth or onto the skull bone under the temporalis muscle. The distal end 702 of the reference electrode lead 701 has a double bend geometry like that of the single branch intra-vestibular electrode array from the active part of the vestibular stimulation electrode. The distal end 702 includes a stopper end 7021 and a stopper collar 7022 that is bent away from the distal end at a first discrete angle. An intra-vestibular electrode branch 7024 is bent away at a second discrete angle from the stopper collar 7022 at a heel end 7023 and has an end tip electrode contact 7025 to form an electrical connection with nearby tissue after surgical implantation. And as with the active intra-vestibular electrode branch, the double bend geometry of the distal end 702 prevents intra-surgical over-insertion and post-surgical migration, and ensures that the implanted part of the distal end 702 will be parallel to the vestibular canal after implantation.

In specific embodiments, the double bend geometry need not necessarily have to end up in parallel with either the vestibular canal or the extra-vestibular lead. Rather, any desired angles are achievable depending on the preferred insertion angle. The angles of the double bend geometry can be adjusted either by design, by shape memory, or by manual bending by the surgeon according to his or her needs.

To Applicant's knowledge, so far no existing vestibular stimulation electrode has used such a double bend structure. FIG. 8A shows an example of a single bend stimulation electrode branch 804 being inserted through a hole drilled in the bone 802 between the destination ampulla 803 and the adjacent semicircular canal 801. FIG. 8B shows another example of another stimulation electrode branch 805 being inserted through a hole drilled in the bone 802 further back in the bone 802 of the semicircular canal 801. In both cases, the inserted part of the electrode branch will not be in parallel with the semicircular canal 801. This makes dubious any claims that such electrode geometries do not compress the membranous labyrinth simply by virtue of having a thin diameter electrode. With a relatively large drilled opening in the bone 802 of the semi-circular canal 801, the insertion angle of the electrode branch can be reduced, but to minimize insertion trauma and the risk of post-surgical inflammation, a smaller opening may be preferred.

A double bend structure electrode 904 as shown in FIG. 9 allows insertion parallel to the canal 901 through a relatively small opening in the bone 902 of the canal 901 into the destination ampulla 903. Note that the location of the opening in the canal 901 will define the insertion depth of the double bend structure electrode 904 and any surgical variation in the location of the opening directly affect the insertion depth. On the other hand with the help of a good surgical technique and well-defined anatomical landmarks the surgical variation can be reduced to a small value which will result in a well-defined insertion depth. The surgical variance and anatomical tolerances can be compensated (at least in part) by switching between the different electrode contacts of the inserted electrode branch.

Although various exemplary embodiments of the invention have been disclosed, it should be apparent to those skilled in the art that various changes and modifications can be made which will achieve some of the advantages of the invention without departing from the true scope of the invention.

What is claimed is:

1. A vestibular stimulation electrode lead for conducting electrical stimulation signals generated by an implanted vestibular stimulation module, the electrode lead comprising:

an extra-vestibular lead branch configured for carrying the stimulation signals from the stimulation module to a vestibular entry location in an outer surface of a vestibular canal;

a distal end of the lead branch bifurcating into a single array branch and a double array branch;

wherein the single array branch forms a stopper collar by bending away at a first discrete angle from the single array branch to penetrate into the vestibular canal at the vestibular entry location, and an intra-vestibular electrode array bends away at a second discrete angle from the stopper collar along a line parallel to the lead branch so as to fit within the vestibular canal and having an outer surface with one or more electrode contacts for delivering the stimulation signals to vestibular neural tissue at a target location within a vestibular structure; and wherein the double array branch comprises a base hub and stopper bridge that form a forked shape with two intra-vestibular branch arrays located adjacent to each other, each intra-vestibular branch array having:

i. one or more electrode contacts for delivering the stimulation signals to vestibular neural tissue, and ii. an end bump configured to limit post-surgical outward withdrawal of the intra-vestibular branch array; and wherein the single branch intra-vestibular electrode array and double branch intra-vestibular branch arrays are pre-shaped so that once one of the arrays is implanted, the other arrays will automatically be close to their insertion location.

2. The electrode lead according to claim 1, wherein the discrete angles of the single array branch form a geometry of the stopper collar and intra-vestibular electrode array that limits insertion of the intra-vestibular electrode array of the single array branch beyond the target location within the vestibular canal.

3. The electrode lead according to claim 1, wherein the intra-vestibular electrode array of the single array branch has at least three electrode contacts.

4. The electrode lead according to claim 1, wherein the electrode lead forms a non-chiral shape.

5. A vestibular implant system having at least one electrode lead according to any one of claims 1-3 and 4.

6. An electrode lead according to claim 1, wherein the bifurcating between the single array branch and the double array branch forms a 120° angle.

* * * * *